United States Patent [19]
Kaiser et al.

[11] 3,966,770
[45] June 29, 1976

[54] 4-HYDROXY-α-[(3,4-METHYLENEDIOXYPHENYL)ISOPROPYL-AMINOETHYL]-3-(METHYLSULFONYLME-THYL)BENZYL ALCOHOL

[75] Inventors: Carl Kaiser, Haddon Heights, N.J.; Stephen T. Ross, Berwyn, Pa.

[73] Assignee: SmithKline Corporation, Philadelphia, Pa.

[22] Filed: Mar. 25, 1975

[21] Appl. No.: 561,828

[52] U.S. Cl............................ 260/340.5; 424/282
[51] Int. Cl.$^2$....................................... C07D 317/44
[58] Field of Search................ 260/340.5, 340.5 R; 424/282

[56] References Cited
UNITED STATES PATENTS

| | | | |
|---|---|---|---|
| 3,341,584 | 9/1967 | Larsen et al. | 260/340.5 |
| 3,711,545 | 1/1973 | Kaiser et al. | 260/340.5 |

OTHER PUBLICATIONS
Collin et al., Journ. Med. Chem., vol. 13, No. 4, 1970, pp. 674–680.

*Primary Examiner*—Ethel G. Love
*Attorney, Agent, or Firm*—Joseph A. Marlino; Richard D. Foggio; William H. Edgerton

[57] ABSTRACT

4-Hydroxy-α-[(3,4-methylenedioxyphenyl)isopropylaminomethyl]-3-(methylsulfonylmethyl)benzyl alcohol having β-adrenergic stimulant activity, particularly as a selective bronchodilator, is prepared from 4-hydroxyacetophenone by conversion to 3-methylsulfonylmethylacetophenone, bromination and conversion of this phenone to the phenylglyoxal and treatment of the resulting glyoxal derivative with 3,4-methylenedioxyphenylisopropylamine followed by simultaneous reduction of the imine and ketone moieties and catalytic hydrogenation to remove the benzyl group.

4 Claims, No Drawings

4-HYDROXY-α-[(3,4-METHYLENEDIOXY-PHENYL)ISOPROPYLAMINOETHYL]-3-(METHYLSULFONYLMETHYL)BENZYL ALCOHOL

This invention relates to a novel 4-hydroxy-α-[(3,4-methylenedioxyphenyl)isopropylaminomethyl]-3-(methylsulfonylmethyl)benzyl alcohol which has useful pharmacodynamic activity. More specifically, the compound of this invention has utility as a β-adrenergic stimulant with relatively greater activity on respiratory smooth muscle than on cardiac muscle. Therefore this compound has direct bronchodilator action with minimal cardiac stimulation as demonstrated in standard pharmacological test procedures.

The compound of this invention is represented by the following structural formula:

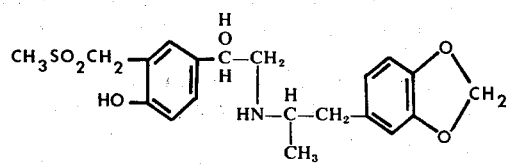

FORMULA 1

Two in vitro test systems used for determining selective β-stimulant activity are: (1) effect on spontaneous tone of guinea pig tracheal chain preparations as a measure of β-stimulant (direct relaxant) effect on airway smooth muscle, and (2) effect on rate of spontaneously beating right atria of the guinea pig as a measure of β-stimulant effect on cardiac muscle. The compound of this invention has selective bronchodilating properties since it is active in (1) above at a dose lower than is required in (2) above resulting in a positive separation ratio. The absolute separation ratio is an indication of the difference between a dose that produces bronchodilation in higher animal studies and a dose that will produce direct increase in cardiac rate. Since cardiac involvement is usually associated with patients suffering from bronchitis, emphysema and other similar disease states, any cardiac rate increase is considered a deleterious or toxic side effect.

The compound of this invention has an unusually large separation between activity on tracheal chain and atria muscle which would not have been expected from previous structure activity studies. For example, Table 1 compares the novel compound of this invention with known and closely related bronchodilators.

It will be noted from the results set forth in Table 1 that the compound C claimed herein is a potent β-adrenergic stimulant having an extraordinarily large separation between activity on tracheal and cardiac muscle which results in a bronchodilator practically devoid of potential cardiac rate side effects. This separation could not have been predicted from similar data obtained with either a methylsulfonylmethyl (compound B) or a methylenedioxyphenyl (compound A) substituted derivative.

The compound of this invention may be used in the form of a pharmaceutically acceptable acid addition salt having the utility of the free base. Such salts, prepared by methods well known to the art, are formed with both inorganic or organic acids, for example: maleic, fumaric, benzoic, ascorbic, pamoic, succinic, bismethylenesalicylic, methanesulfonic, ethanedisulfonic, acetic, oxalic, propionic, tartaric, salicylic, citric, glyconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

TABLE 1

| Compound | $ED_{50}$-trachea (mcg/ml.) | $ED_{25}$-atria (mcg/ml.) | Absolute Separation Ratio ($ED_{25}/ED_{50}$) |
|---|---|---|---|
| Isoproterenol | 0.0015 | 0.00073 | 0.48 |
| A.* | 0.00042 | 0.0014 | 3.3 |
| B.** | 0.0051 | 8.28 | 1620 |
| C. | 0.0068 | inactive at 90.0 | >13235 |

*Disclosed in Br. J. Pharmac. Chemother. (1968) 33, 552-559
**Disclosed in Belgium Pat. No. 796,894 which issued on September 17, 1973.

Further the compound of this invention contains two asymmetric carbon atoms. Thus, it exists as separable diastereoisomers. The separation can be achieved by fractional recrystallization of an appropriate salt such as, for example, a hydrochloride, hydrobromide, maleate, fumarate, citrate or cyclohexylsulfamate, from a solvent such as water, methanol, ethanol, isopropanol, ethyl acetate, or ether either as a single solvent or in combination. The diastereoisomers may also be separated by chromatographic methods, using either column or high pressure liquid phase chromatography.

Each of the separated diastereoisomers is resolvable into $d$ and $l$ optical isomers. The most convenient means for accomplishing resolution is by recrystallization of a salt of the isolated diastereoisomeric base with an optically active acid, such as for example, tartaric, dibenzoyltartaric, di-(p-toluoyl)tartaric camphorsulfonic, mandelic, N-acetyltryptophane or malic, from an appropriate solvent such as for example, water, methanol, ethanol, isopropanol, ethyl acetate, ether, and combinations thereof. The mother liquors from such separation may be reconverted to base in the usual way, i.e., neutralization of a solution or suspension of the salt used for resolution in water with aqueous ammonia, followed by extraction of the base into ethyl acetate. After being dried and concentrated, the remaining base may be converted to the salt with the enantiomeric acid. This salt is then recrystallized from the same solvent system initially employed to give the second enantiomer. Unless otherwise specified in the description and accompanying claims, it is intended to include all isomers, whether separated or mixtures thereof.

The compound of this invention is prepared by chloromethylating 4-hydroxyacetophenone with formaldehyde and hydrochloric acid. The acetophenone is then treated with the sodium or magnesium salt of methylsulfinic acid to yield the methylsulfonylmethyl derivative. The later is brominated and the resultant 2-bromoacetophenone is reacted with dimethylsulfoxide to give the corresponding glyoxal. This derivative is treated with 3,4-methylenedioxyphenylisopropylamine and the resultant iminoacetophenone derivative is reduced to the corresponding benzyl alcohol and hydrogenated catalytically, preferably with palladium-on-carbon, to give 4-hydroxy-α-[(3,4-methylenedioxyphenyl)-isopropylaminomethyl]-3-(methylsulfonylmethyl)benzyl alcohol.

The compounds of this invention may be administered orally or parenterally in conventional dosage unit forms such as tablets, capsules, injectables, aerosols, or the like, by incorporating the appropriate dose of a compound of Formula 1 or an acid addition salt thereof with carriers according to accepted pharmaceutical practices.

Preferably a compound or an acid addition salt thereof is administered orally to an animal organism in a tablet or capsule comprising an amount sufficient to produce β-adrenergic stimulant activity. Each dosage unit will contain the active ingredient in an amount of about 1 mg. to about 40 mg., preferably from about 3 mg. to about 20 mg. Advantageously equal doses will be administered 2 to 4 times daily with the daily dosage regimen being about 2 mg. to about 160 mg., preferably from about 6 mg. to about 80 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

Of particular applicability is an aerosol dispensing system wherein the active medicament is incorporated with Freon (fluorohydrocarbon) or other inert propellant in an aerosol container. Such an aerosol system will deliver a metered dose of about 100 mcg. to about 650 mcg., administered once or twice at a time as needed.

The following example is not limiting but merely illustrative of a procedure for the preparation of the compound of this invention.

EXAMPLE

To a mixture of 260 ml. of 37% formaldehyde and 1800 ml. of concentrated hydrochloric acid is added 400 g. of 4'-hydroxyacetophenone at a temperature of about 45°C. The mixture is maintained at 50°C. for two hours, filtered, and washed with water to give 3'-chloromethyl-4'-hydroxyacetophenone, m.p. 154° C. dec.

A mixture of 40 g. of 3'-chloromethyl-4'-hydroxyacetophenone and 26 g. of magnesium methyl sulfinate in 500 ml. of ethanol is refluxed with stirring for 3 hours. The reaction mixture is then concentrated in vacuo. The resultant oil is redissolved in chloroform and washed with water. The chloroform is dried and evaporated to give 4'-hydroxy-3'-methylsulfonylmethylacetophenone, m.p. 206.5°–208.5° C.

A mixture of 14.0 g. of 4'-hydroxy-3'-methylsulfonylmethylacetophenone, 9.3 g. of potassium carbonate, 7.8 ml. of benzyl chloride and a catalytic amount of sodium iodide in 250 ml. of acetone and 250 ml. of water is refluxed with stirring for 16 hours. The acetone is removed and the aqueous phase is extracted with chloroform, washed with water, dried and evaporated to yield an oil which is recrystallized in 2-propanol to give crystalline 4'-benzyloxy-3'methylsulfonylmethylacetophenone, m.p. 94°–97° C.

To a stirred solution of 7.7 g. of 4'-benzyloxy-3'-methylsulfonylmethylacetophenone and 2.15 g. of 2-pyrrolidinone in 300 ml. of tetrahydrofuran is added 12.5 g. of pyrrolidinone hydrotribromide (PHT) and the stirring is continued for 56 hours at room temperature. The mixture is filtered and the filtrate concentrated in vacuo to give an oil which crystallizes upon standing. The crystals are redissolved in chloroform. The chloroform solution is washed with water, dried and concentrated to yield a solid which is recrystallized from acetonitrile to give 4'-benzyloxy-2-bromo-3'-methylsulfonylmethylacetophenone, m.p. 143°–144° C.

The latter (4.0 g.) is dissolved in 30 ml. of dimethylsulfoxide and permitted to stand 3 days. The solution is then added dropwise to ice water. The resultant precipitate is filtered, treated with acetone and the solution is dried and concentrated to yield 4-benzyloxy-3-(methylsulfonylmethyl)phenylglyoxal hydrate, m.p. 108°–111°C.

A mixture of 1.95 g. of 3,4-methylenedioxyphenylisopropylamine and 4.0 g. of the above phenylglyoxal in 100 ml. of methanol is stirred at 25° C. for sixteen hours. The solution is then filtered resulting in the crystallization of a white solid. The mixture is concentrated in vacuo to yield 4'-benzyloxy-α-[(3,4-methylenedioxyphenyl)isopropylamino]-3'-(methylsulfonylmethyl)acetophenone. The crystalline acetophenone (4.0 g.) is added to 120 ml. of ethanol and 1.5 g. of sodium borohydride is added in portions. The formed slurry is dissolved and the reaction mixture is stirred at 25° C. overnight. The mixture is made acidic with ethereal hydrochloric acid and concentrated in vacuo. The residue is partitioned between dilute hydrochloric acid and chloroform. The chloroform layer is filtered to yield 4-benzyloxy-α-[(3,4-methylenedioxyphenyl)-isopropylaminomethyl]-3-(methylsulfonylmethyl)benzyl alcohol hydrochloride as an amorphous solid which is then dissolved in 100 ml. of methanol containing 1.0 g. of 10% palladium-on-carbon and hydrogenated on a Parr apparatus at ambient temperature using an initial hydrogen pressure of 60 psi. The reaction mixture is filtered and the filtrate is concentrated in vacuo. The residue is crystallized with ether-methanol to yield 4-hydroxy-α-[(3,4-methylenedioxyphenyl)isopropylaminomethyl]-3-(methylsulfonylmethyl)benzyl alcohol hydrochloride, m.p. 182.0°–183.5° C.

What is claimed is:
1. A chemical compound of the formula:

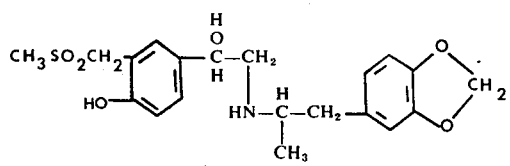

or a pharmaceutically acceptable acid addition salt of said compound.

2. A pharmaceutical composition having β-adrenergic stimulant activity in dosage unit form comprising a pharmaceutical carrier and a β-adrenergic stimulating effective amount of a chemical compound of the formula:

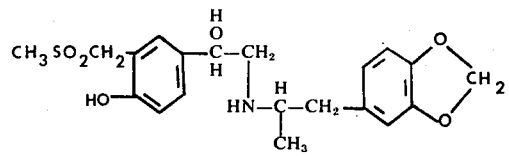

or a pharmaceutically acceptable acid addition salt of said compound.

3. A method of producing β-adrenergic stimulant activity which comprises administering internally to an animal requiring bronchodilation an amount sufficient to produce said activity of a chemical compound of the formula:

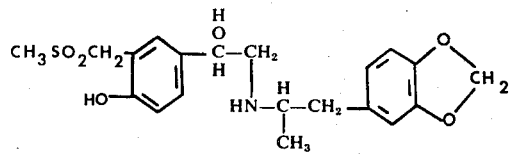

or a pharmaceutically acceptable acid addition salt of said compound.

4. A chemical compound according to claim 1 in the form of a hydrochloride salt.

* * * * *

UNITED STATES PATENT AND TRADEMARK OFFICE
CERTIFICATE OF CORRECTION

PATENT NO. : 3,966,770

DATED : June 29, 1976

INVENTOR(S) : Carl Kaiser and Stephen T. Ross

It is certified that error appears in the above-identified patent and that said Letters Patent are hereby corrected as shown below:

Title Page, Title reads:

"4-HYDROXY-α-[(3,4-METHYLENEDIOXYPHENYL)ISOPROPYLAMINO-ETHYL]-3-(METHYLSULFONYLMETHYL)BENZYL ALCOHOL"

Title should read:

"4-HYDROXY-α-[(3,4-METHYLENEDIOXYPHENYL)ISOPROPYLAMINO-METHYL]-3-(METHYLSULFONYLMETHYL)BENZYL ALCOHOL"

Column 1, lines 1 to 3, reads:

"4-HYDROXY-α-[(3,4-METHYLENEDIOXYPHENYL)ISOPROPYLAMINO-ETHYL]-3-(METHYLSULFONYLMETHYL)BENZYL ALCOHOL"

Column 1, lines 1 to 3, should read:

"4-HYDROXY-α-[(3,4-METHYLENEDIOXYPHENYL)ISOPROPYLAMINO-METHYL]-3-(METHYLSULFONYLMETHYL)BENZYL ALCOHOL"

Signed and Sealed this

Seventh Day of September 1976

[SEAL]

Attest:

RUTH C. MASON
*Attesting Officer*

C. MARSHALL DANN
*Commissioner of Patents and Trademarks*